United States Patent
Buelna

(10) Patent No.: US 10,357,302 B2
(45) Date of Patent: Jul. 23, 2019

(54) RENAL NERVE DENERVATION VIA THE RENAL PELVIS

(75) Inventor: Terrence J. Buelna, Santa Barbara, CA (US)

(73) Assignee: Verve Medical, Inc., Scottsdale, AZ (US)

( * ) Notice: Subject to any disclaimer, the term of this patent is extended or adjusted under 35 U.S.C. 154(b) by 8 days.

(21) Appl. No.: 13/547,486

(22) Filed: Jul. 12, 2012

(65) Prior Publication Data

US 2013/0178824 A1   Jul. 11, 2013

Related U.S. Application Data

(60) Provisional application No. 61/506,976, filed on Jul. 12, 2011.

(51) Int. Cl.
*A61B 18/00* (2006.01)
*A61B 18/14* (2006.01)
(Continued)

(52) U.S. Cl.
CPC .............. *A61B 18/00* (2013.01); *A61B 18/08* (2013.01); *A61B 18/1492* (2013.01); *A61B 18/1815* (2013.01); *A61M 25/10* (2013.01); *A61N 7/022* (2013.01); *A61B 2018/0016* (2013.01); *A61B 2018/0022* (2013.01); *A61B 2018/00267* (2013.01); *A61B 2018/00291* (2013.01); *A61B 2018/00404* (2013.01);
(Continued)

(58) Field of Classification Search
CPC . A61B 18/00; A61B 18/1492; A61B 18/1815; A61B 18/08; A61B 2018/00404; A61B 2018/00267; A61B 2018/00511; A61B 2018/00291; A61B 2018/046; A61B 2018/044; A61B 2018/00434; A61B 2018/0016; A61B 2018/1475; A61B 2018/0022; A61B 2018/143; A61N 7/002; A61M 25/10
USPC .......................................................... 600/3
See application file for complete search history.

(56) References Cited

U.S. PATENT DOCUMENTS 5,370,677 A * 12/1994 Rudie .................... A61B 18/18
606/41
6,607,477 B1   8/2003 Longton et al.
(Continued)

FOREIGN PATENT DOCUMENTS

CN   101084038 A   12/2007
CN   101426551 A   5/2009
(Continued)

OTHER PUBLICATIONS

Office action dated Sep. 25, 2014 for U.S. Appl. No. 13/217,233.
(Continued)

*Primary Examiner* — Kaylee R Wilson
(74) *Attorney, Agent, or Firm* — Wilson Sonsini Goodrich & Rosati

(57) ABSTRACT

Apparatus, systems, and methods provide access to the renal pelvis of a kidney to treat renal nerves embedded in tissue surrounding the renal pelvis. Access to the renal pelvis may be via the urinary tract or via minimally invasive incisions through the abdomen and kidney tissue. Treatment is effected by exchanging energy, typically delivering heat or extracting heat through a wall of the renal pelvis, or by delivering active substances.

3 Claims, 14 Drawing Sheets

(51) Int. Cl.
*A61M 25/10* (2013.01)
*A61N 7/02* (2006.01)
*A61B 18/08* (2006.01)
*A61B 18/18* (2006.01)
*A61B 18/04* (2006.01)

(52) U.S. Cl.
CPC ............... *A61B 2018/00434* (2013.01); *A61B 2018/00511* (2013.01); *A61B 2018/044* (2013.01); *A61B 2018/046* (2013.01); *A61B 2018/143* (2013.01); *A61B 2018/1475* (2013.01)

(56) References Cited

U.S. PATENT DOCUMENTS

| | | |
|---|---|---|
| 7,653,438 B2 | 1/2010 | Deem et al. |
| 7,717,948 B2 | 5/2010 | Demarais et al. |
| 2002/0048310 A1 | 4/2002 | Heuser |
| 2003/0216792 A1 | 11/2003 | Levin et al. |
| 2006/0235474 A1 | 10/2006 | Demarais |
| 2006/0276852 A1 | 12/2006 | Demarais et al. |
| 2007/0129720 A1 | 6/2007 | Demarais et al. |
| 2008/0086073 A1* | 4/2008 | McDaniel ................ 604/22 |
| 2008/0228209 A1 | 9/2008 | DeMello et al. |
| 2009/0192485 A1 | 7/2009 | Heuser |
| 2010/0168731 A1* | 7/2010 | Wu et al. ................ 606/33 |
| 2011/0015648 A1 | 1/2011 | Alvarez et al. |
| 2011/0060324 A1 | 3/2011 | Wu et al. |
| 2011/0104061 A1 | 5/2011 | Seward |
| 2011/0301662 A1 | 12/2011 | Bar-Yoseph et al. |
| 2012/0109021 A1 | 5/2012 | Hastings et al. |
| 2013/0053732 A1 | 2/2013 | Heuser |
| 2014/0107639 A1* | 4/2014 | Zhang ............... A61B 18/1492 606/33 |

FOREIGN PATENT DOCUMENTS

| | | |
|---|---|---|
| CN | 101583323 A | 11/2009 |
| DE | 19701840 A1 | 11/1997 |
| EP | 2747830 A1 | 7/2014 |
| WO | WO 91/03996 A1 | 4/1991 |
| WO | WO-2007078997 A2 | 7/2007 |
| WO | WO 2009/097294 A1 | 8/2009 |
| WO | WO 2010/067360 A2 | 6/2010 |
| WO | WO 2010/067360 A3 | 9/2010 |
| WO | WO 2011/046880 A2 | 4/2011 |
| WO | WO 2011/053757 A1 | 5/2011 |
| WO | WO 2011/082278 A1 | 7/2011 |
| WO | WO 2011/112400 A1 | 9/2011 |
| WO | WO 2012/170482 A1 | 12/2012 |

OTHER PUBLICATIONS

Office action dated Feb. 27, 2013 for U.S. Appl. No. 13/217,233.
Office action dated Jun. 14, 2013 for U.S. Appl. No. 13/217,233.
International search report and written opinion dated Oct. 2, 2012 for PCT/US2012/046511.
European search report and opinion dated Dec. 2, 2014 for EP Application No. 12811672.0.
International search report and written opinion dated Dec. 17, 2013 for PCT/US2012/051950.
"European search report dated Mar. 9, 2015 for EP Application No. 12825105.5."
Davidson, et al. Interventional approaches for resistant hypertension. Curr Opin Nephrol Hypertens. 2012; 21(5):475-480.
Office action dated Apr. 22, 2015 for U.S Appl. No. 13/217,233.

* cited by examiner

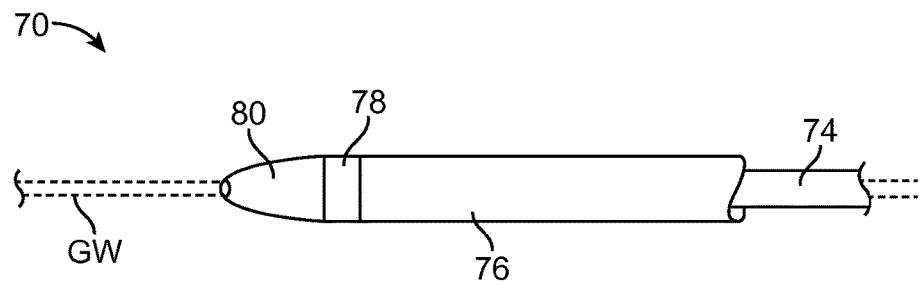
FIG. 7A
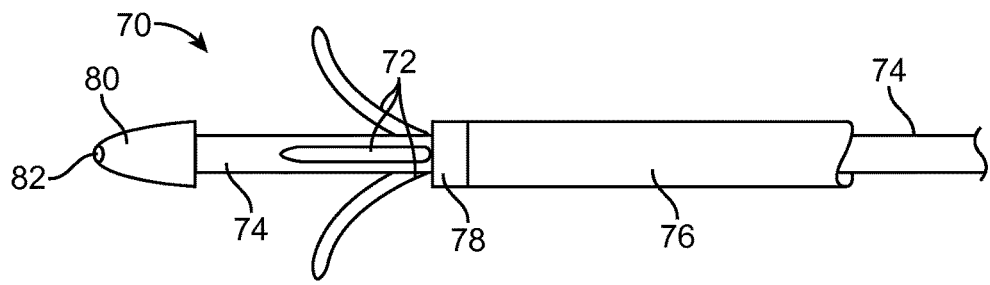
FIG. 7B
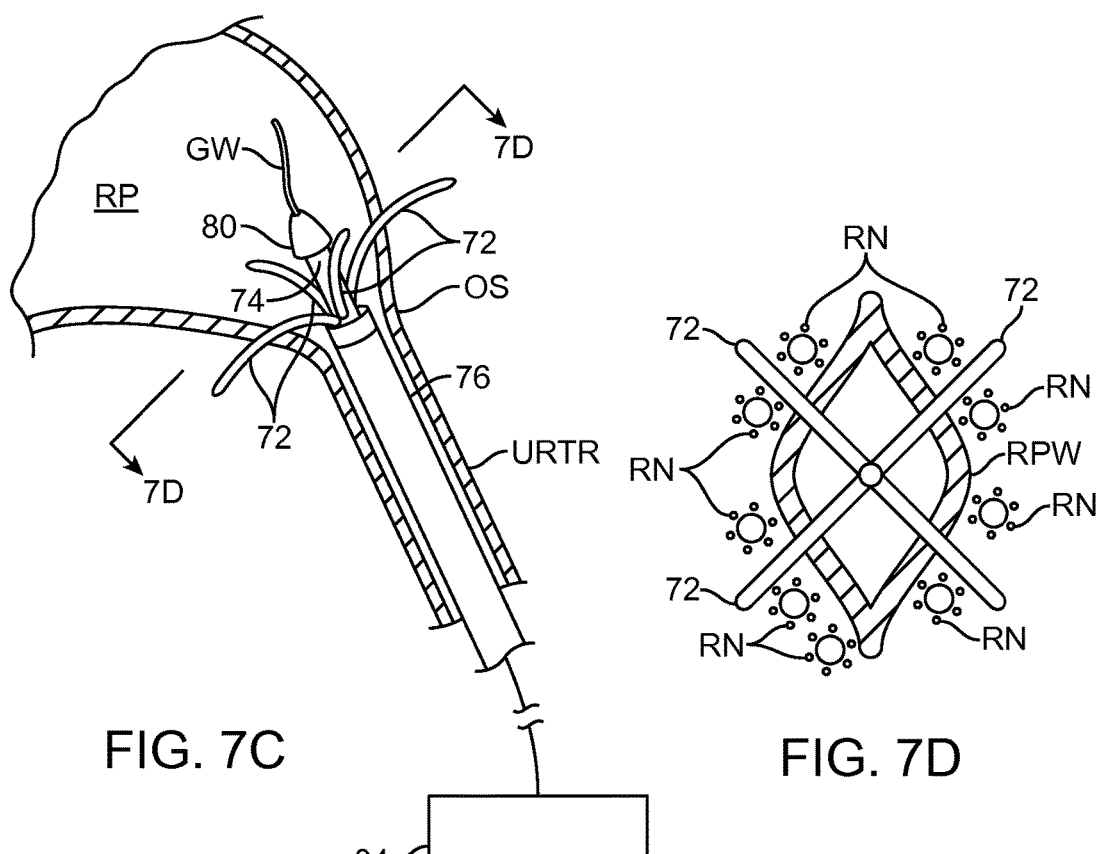
FIG. 7C
FIG. 7D
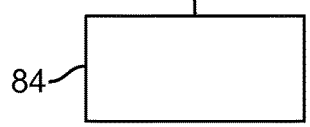

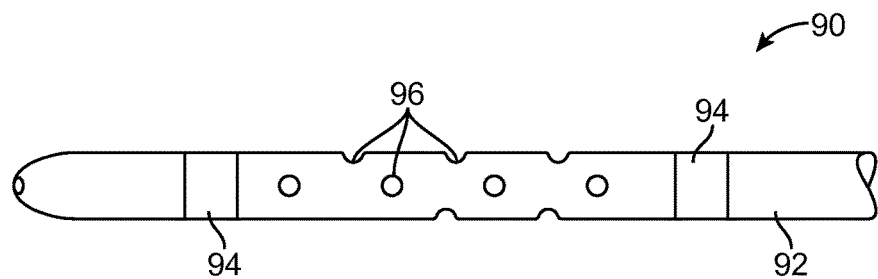
FIG. 8A
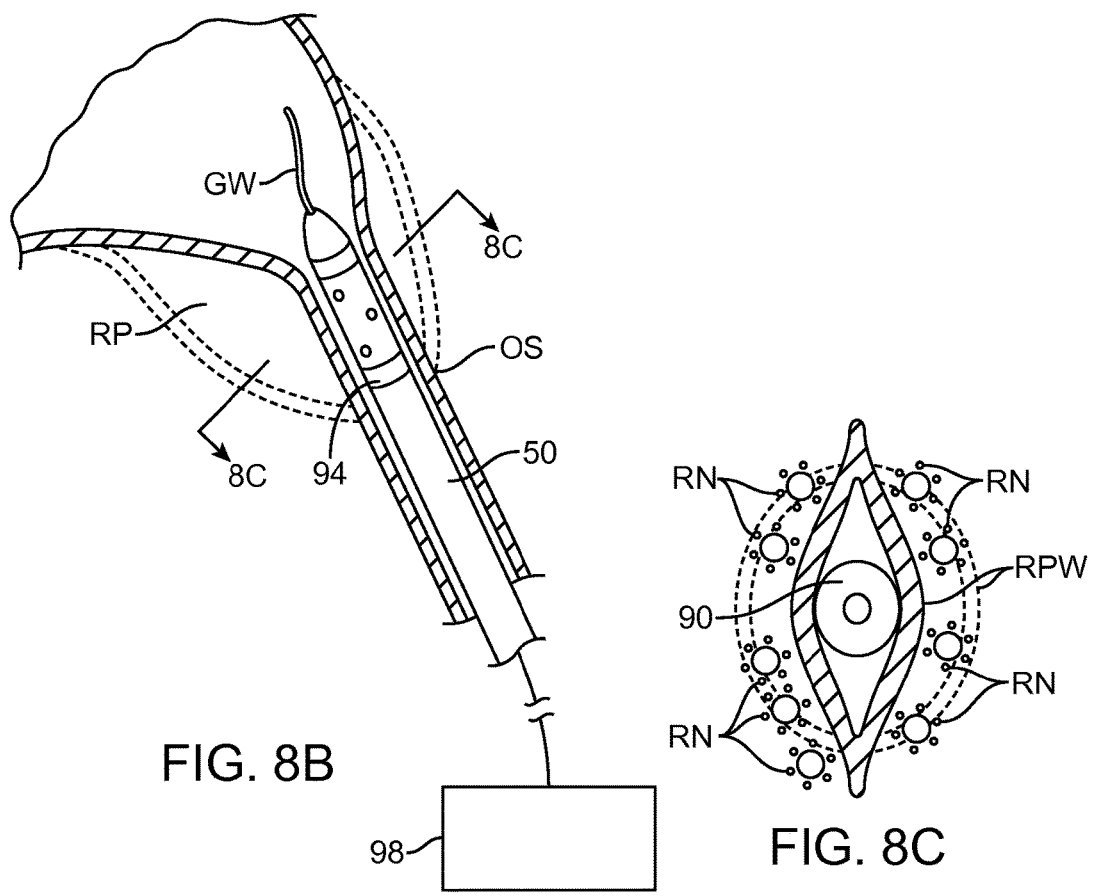
FIG. 8B
FIG. 8C

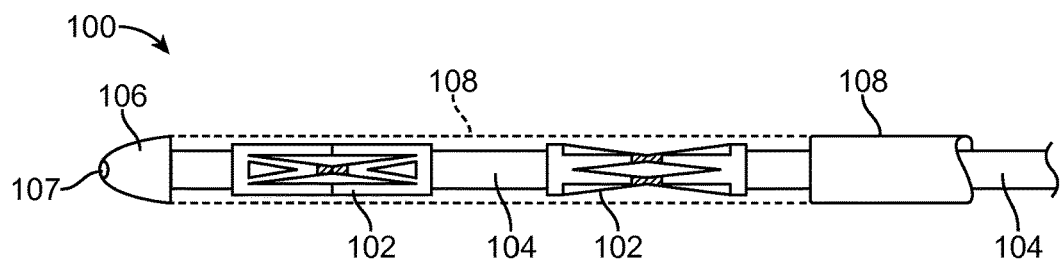
FIG. 9A
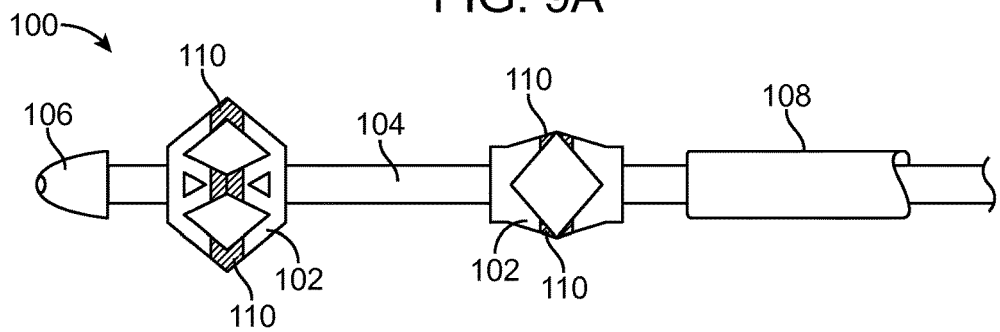
FIG. 9B
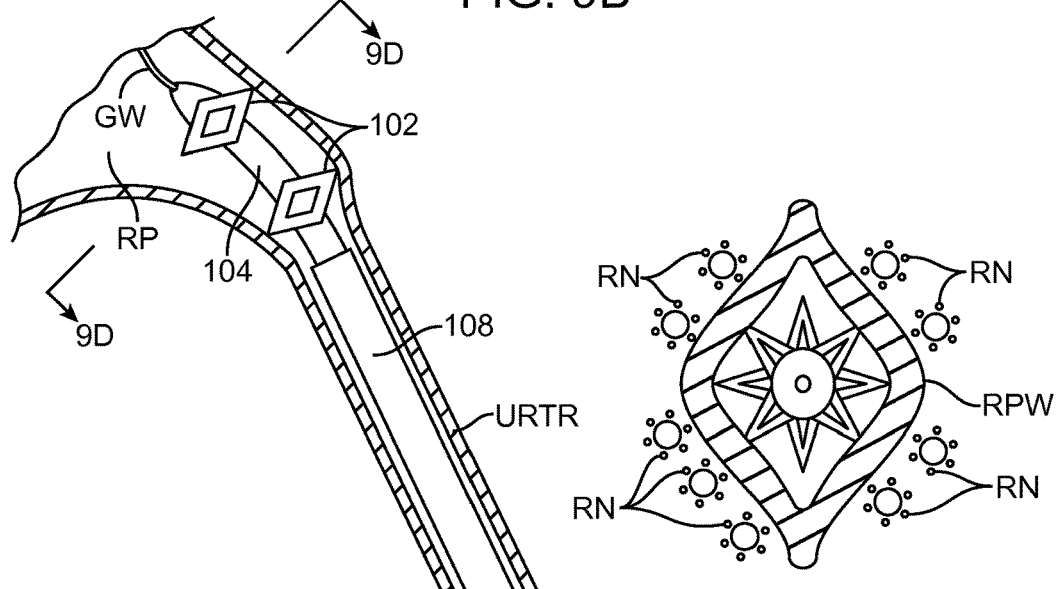
FIG. 9C
FIG. 9D

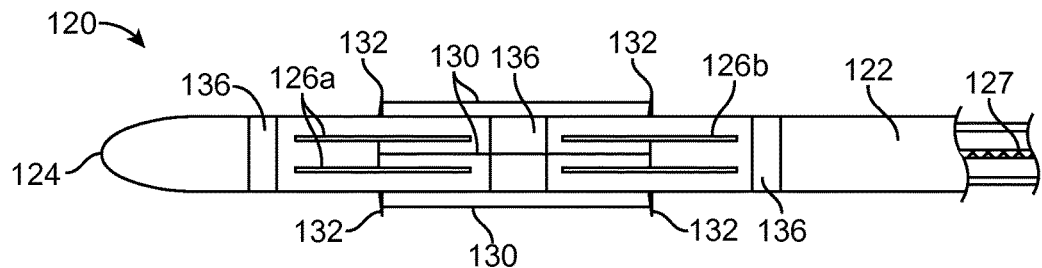
FIG. 10A
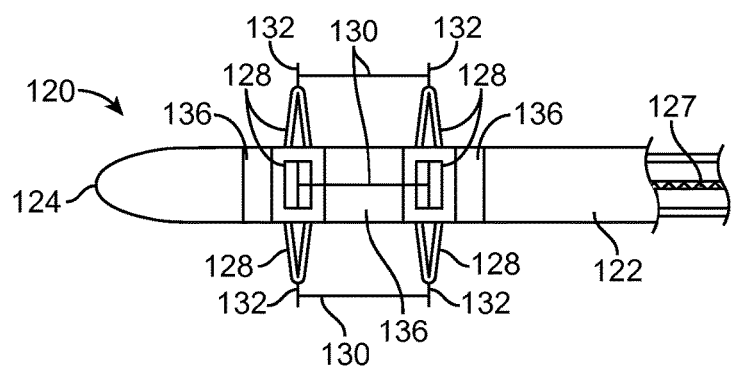
FIG. 10B
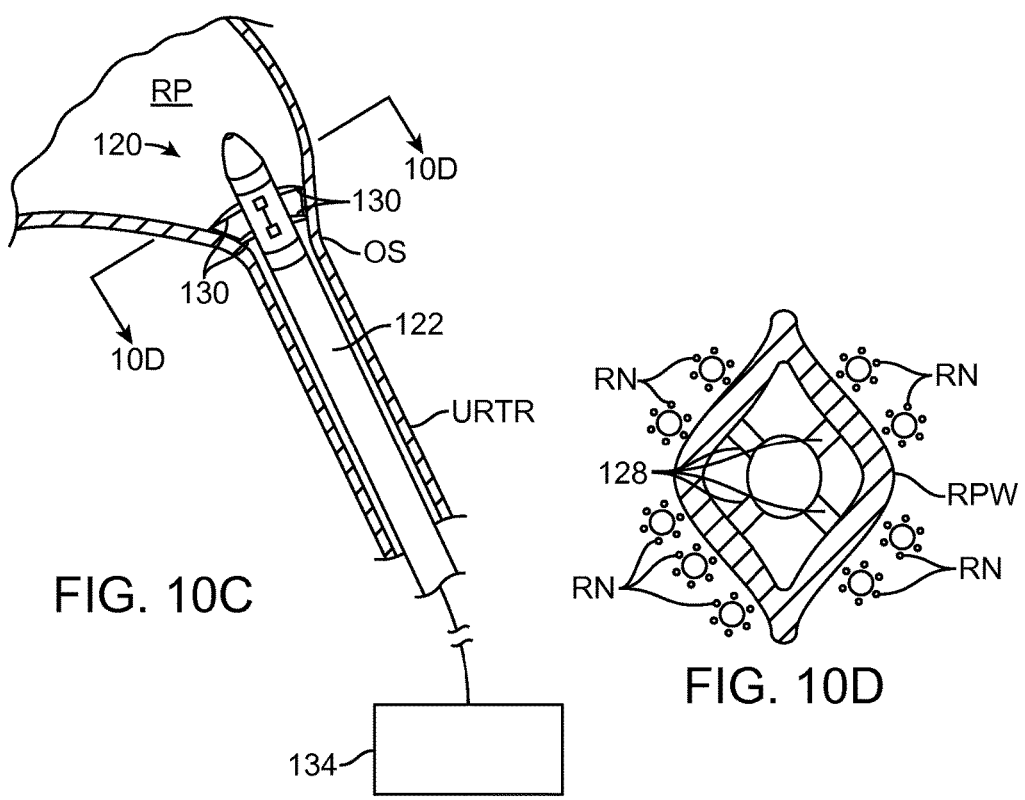
FIG. 10C
FIG. 10D

RENAL NERVE DENERVATION VIA THE RENAL PELVIS

CROSS-REFERENCES TO RELATED APPLICATIONS

The present application claims the benefit of U.S. Provisional Patent Application No. 61/506,976, filed Jul. 12, 2011, the entire contents of which are incorporated herein by reference.

BACKGROUND OF THE INVENTION

1. Field of the Invention

The present invention relates generally to medical devices, systems, apparatus, and methods for modifying nerve function and treating disease. More particularly, the present invention relates to methods and apparatus for exchanging energy or delivering active agents through the renal pelvis to modify sympathetic nerve activity in the adventitia of arteries and/or veins that surround the external surface of the renal pelvis in the kidney and in the afferent and efferent nerves within the muscles layers, urothelium and submucosa of the renal pelvis.

Hypertension, or high blood pressure, is a significant and growing health risk throughout the world. Hypertension can be caused by hyperactive renal sympathetic nerves which extend adjacent to the outside of the arteries and veins leading to a patient's kidney as well as within the wall of the renal pelvis. Renal nerve activity can be a significant cause of systemic hypertension, and it has long been known that disrupting renal nerve function can reduce blood pressure. More recently, hypertension therapies based on disrupting the renal nerves surrounding the renal arteries leading to the kidney (renal denervation) have been proposed and are described in the medical and patent literature.

Heretofore, most of the proposed renal denervation therapies have utilized an intravascular approach where a catheter is introduced into the arterial system and advanced to the main renal artery leading to the left or right kidney. Once located at a desired target site within the main renal artery, the catheter is used to deliver radiofrequency energy, heat, drugs, or the like to disrupt the function of the renal nerves which surround the artery. While effective, these techniques present a risk of injury to the renal artery and suffer from all the known disadvantages associated with intravascular access and therapies.

For these reasons, it would be desirable to provide alternative protocols and apparatus for accessing the renal nerves for the purpose of performing denervation or other renal nerve function disruptions which do not rely on intravascular access and which are not performed in the main renal artery leading to the kidney. It would be further desirable if such protocols and apparatus could be performed minimally invasively, would present a reduced risk of injury and trauma to the patient, were economical, and could be performed using simplified and scalable methods. In particular, it would be desirable to provide methods and apparatus for renal nerve denervation and modulation that could be performed using a natural orifice surgery. At least some of these objectives will be met by the inventions described herein below.

2. Description of the Background Art

U.S. Patent Publication No. 2011/0060324 describes apparatus, systems, and methods for performing thermally-induced renal neuromodulation by intravascular access. U.S. Patent Publication No. 2011/0104061 describes apparatus, systems, and methods for active agents to the renal arteries for achieving renal denervation. Published PCT Application WO2010/067360 describes methods and apparatus for modifying blood pressure and kidney function via stimulation of the urinary tract by stimulating the renal nerves.

BRIEF SUMMARY OF THE INVENTION

The present invention provides apparatus, systems, and methods for disrupting, inhibiting, denervating and/or modulating the activity of renal nerves present in a patient's kidney by exchanging energy or delivering active agents or substances to the renal nerves which lie within the wall of the renal pelvis or adjacent to the renal pelvis within the kidney. Most commonly, such renal denervation and/or modulation will be for the purpose of reducing blood pressure in patients suffering from and/or diagnosed diagnosed with hypertension, but the methods and apparatus of the present invention could be used for treating patients diagnosed with other conditions as described below. The energy exchange or agent delivery is effected through a wall of the renal pelvis using an effector which has been positioned within the interior of the renal pelvis. The renal blood vessels, including the renal arteries and to a lesser extent the renal veins, enter the kidney in a branching network from the main renal artery and main renal vein leading to the kidney. The renal nerves are present in the adventitial tissue surrounding these branching blood vessels as well as in the tissue bed adjacent to the external wall of the renal pelvis. The renal nerves are also in the wall of the renal pelvis in the form of a dense nerve matrix consisting of both afferent and efferent nerves between the muscle layers as well as within the endothelium and submucosa.

The wall of the renal pelvis is a particularly rich source for afferent sensory nerves which are found in the urothelium which lies immediately adjacent to the renal pelvis. They are also found in rich supply in the intermediate submucosale layer which is closest to the urothelium. The renal pelvis wall is also a source for efferent nerves which are found in both the intermediate and outer submucosale layers. Thus, the treatments of the present invention which exchange energy or deliver active agents from the renal pelvis may be particularly effective in treating the afferent sensory nerves which are presently believed to be principally responsible for the reduction of hypertension.

The present invention relies on introducing or advancing the effector into the interior of the renal pelvis by a minimally invasive approach or access. Usually the access will be through the urinary tract and thus not require percutaneous penetration (and thus may be performed as a "natural orifice surgery"). Alternatively, the access could be achieved through known laproscopic or other percutaneous techniques relying on access penetrations through the abdominal wall and advancement of tools through the body of the kidney in order to access the hilum and in turn the renal pelvis. Such laproscopic techniques are on the one hand disadvantageous because they require such tissue penetrations but on the other hand are advantageous in that they allow introduction and utilization of large tools under direct visualization which would not be possible using a minimally invasive approach via the urinary tract.

Once in the interior of the renal pelvis, the effector will be used to exchange energy and/or deliver active agents or substances to the wall of the renal pelvis and additionally to the tissue bed surrounding the exterior wall of the renal pelvis to effect nerve denervation or modulation. Often, the effector will be an expandable structure, such as an inflatable balloon or mechanically expandable cage, which can be deployed within the renal pelvis to engage at least a portion of interior wall of the renal pelvis, often engaging the entire interior wall of the renal pelvis. Elements for exchanging energy and/or delivering active substances can be present on the outer wall of such expandable structures or may be present within the interior of such expandable structures in order to generate, exchange, and deliver energy and substances as described in more detail below.

Other embodiments of the effector include tissue-penetrating needles and electrodes for delivering or exchanging energy within the wall of the renal pelvis, radiation-emitting sources, such as radioisotopes, electronic radiation emitters, such as X-ray sources, and the like In preferred embodiments of the present invention, the exchange of energy and/or delivery of active substances will be limited to protect structures within the kidney not surrounding the renal pelvis, such as the papillae, the parenchyma, the pyramids, and the like. The energy exchange and/or active substance delivery may optionally extend into an upper portion or region of the ureter, and in some cases it may be possible to position a microwave antennae, ultrasound transducer, or other energy transmitter entirely within the ureter to direct energy toward the nerves within and adjacent to the renal pelvis, e.g., within the ureteral pelvic junction (UPJ). Limiting the therapies to avoid such sensitive kidney structures surrounding the renal pelvis limits or eliminates damaging such structures and adversely impacting renal function.

Thus, in a first aspect, the present invention provides methods for inhibiting or modulating the function of renal nerves in a patient's kidney. The purpose of the inhibition or modulation could be for treating systemic hypertension, chronic kidney disease, chronic heart disease, sleep apnea, chronic pain, polycystic kidney disease, insulin resistance, obesity, benign prostate hyperplasia, (BPH), or for other purposes. The method is carried out by introducing an effector into an interior of the kidney and exchanging energy and/or delivering active substances from the interior of the kidney through a wall of the renal pelvis to the renal nerves within the pelvic wall as well as surrounding the renal blood vessels within the kidney or UPJ. In many embodiments, the methods will rely on delivering energy to raise the temperature of the renal pelvis and the tissue bed surrounding the blood vessels to a temperature within a target range sufficient to inhibit or destroy nerve function (denervation) typically being in the range from 45° C. to 80° C., usually in the range from 45° C. to 60° C., typically for a time in the range from 3 sec. to 4 minutes, usually from 1 minute to 2 minutes. In such cases, the energy delivery will preferably be directed or limited so that tissue beyond that surrounding the renal pelvis, such as other renal structures including the papillae, the pyramids, and the like, is maintained below a temperature which would adversely affect the tissue function, typically below 45° C. A number of particular methods and devices for delivering energy to raise the tissue temperature are described in more detail below. In other embodiments, the energy exchange may comprise extracting energy from the tissue bed surrounding the blood vessels to cool said tissue bed to the temperature in the range from −10° C. to −100° C., typically from −50° C. to −100° C. Such cooling of the tissue will typically be carried out for a time period in the range from 3 sec. to 4 minutes, usually from 1 minute to 4 minutes. As with heating, the present invention will also limit the cooling of tissue surrounding the renal pelvis to a temperature which will not adversely affect tissue function, typically above −10° C.

The effector may be advanced to the interior of the renal pelvis of the kidney in a variety of ways. Usually, the effector will be advanced through the urinary tract to reach the renal pelvis without the need to penetrate tissue. In such cases, the effector will be disposed on a urinary catheter, typically near a distal end of the catheter, and the urinary catheter will be advanced through the urethra, the bladder, and the ureter to reach the renal pelvis. Techniques for advancing catheters into the renal pelvis are known in the art, for example in connection with delivery of urinary stents to create drainage paths past urinary stones. Usually, an access or guide catheter and/or a guidewire will be placed through the urethra into the bladder to provide an access path to the os of the ureter at an upper end of the bladder. A second catheter carrying the effector will then be advanced through the access or guide catheter and/or over the guidewire and then through the length of the ureter so that the effector is position within the interior of the renal pelvis. The effector will usually be expanded and then be used to exchange energy and/or deliver active substances, as described in greater detail below.

Alternatively, the effector could be advanced to the renal pelvis percutaneously using known laparoscopic and endoscopic techniques. For example, an access trocar may be placed through the patient's abdomen, typically with insufflations of the abdomen to provide a working space. Usually, two, three or even four of such access penetrations will be formed, where one or more of these can be used to introduce the laparoscope or endoscope to visualize the kidney. Tools may then be advanced through others of the access ports in order to penetrate the retroperitoneal space and locate the kidney and to advance the effector through the retroperitoneal space, into the hilum of the kidney, and further into and on the renal pelvis. Once present in the renal pelvis, the effector will be used as described in more detail below in order to achieve the desired therapeutic effect.

A number of specific devices and methods may be employed using the effector in order to denervate, modulate, or inhibit the renal nerves within the wall of the pelvis or surrounding the renal pelvis. For example, the effector may comprise electrodes, typically on an inflatable or expandable structure, and the electrodes may be used to deliver radiofrequency energy across the wall of the renal pelvis to treat the nerves within the wall of the renal pelvis and/or further into the nerves surrounding the renal pelvis to heat the tissue bed surrounding the pelvis to treat the renal nerves. The electrodes may be monopolar, in which case the "active" electrodes on the effector will be connected to one pole of a radiofrequency generator while the other pole will be connected to a dispersive electrode placed on the patient's skin, typically on the small of the back. Alternatively, the radiofrequency electrodes could be bipolar, where one or more electrode pairs (nominally positive and negative) are disposed on the surface of the effector in order to deliver a more localized and higher current density to the tissue surrounding the renal pelvisto treat the nerves within the wall of the renal pelvis and/or further into the nerves surrounding the renal pelvis.

Alternatively, the effector may comprise an antenna to deliver microwave energy to heat the tissue within the wall of the renal pelvis and surrounding the renal pelvis which includes the renal nerves and blood vessels. The microwave antenna may be disposed within the effector since it does not have to contact the tissue along the inner wall of the renal pelvis.

As a still further alternative, the effector may comprise an ultrasound transducer adapted to deliver ultrasound energy through the wall of the renal pelvis into the tissue bed surrounding the renal pelvis. For example, the ultrasound transducer may comprise an unfocused transducer array disposed over a surface continuous with a wall of the renal pelvis. Alternatively, the ultrasound transducer may comprise a high intensity focused ultrasound (HIFU) transducer array present on a structure or assembly within an interior portion of an expandable effector. In such cases, the expandable structure serves to position the ultrasound array relative to the tissue, and the ultrasound array can be arranged to deliver the energy in a direction selected to treat the target tissue bed and nerves. As a still further alternative, external transcutaneous ultrasound can be directed to the hilum and further into the renal pelvis. A target catheter may placed through the urethra, bladder and ureter into the renal pelvis to help direct the treatment.

In a still further alternative, the effector may comprise a convective heat source in order to convectively deliver heat through the wall of the renal pelvis and into the tissue bed and nerves surrounding the pelvis. In a simple configuration, the convective heat source could be hot water or other heat exchange medium, heated either externally or more likely internally using, for example, an electrically resistive heat source.

In a still further example, the effector may comprise a convective cooling source in order to extract heat through a wall of the renal pelvis to cool the wall of the pelvis and the tissue bed surrounding the pelvis which contains the renal nerves and blood vessels. The cooling source may comprise a cryogenic fluid source with an expandable heat-exchanging effector positioned within the renal pelvis. Alternatively, the cooling source could rely on expanding a liquid or gas within the effector to achieve cooling.

In yet another example, the effector may comprise a cage or other support structure adapted to carry a radioactive or other radiation-emitting source. Useful radiation-emitting sources include radioactive "seeds," e.g. radioisotopes having short half lives, as well as x-ray and other electronic radiation sources.

In a second aspect, the present invention provides apparatus and systems for inhibiting, modulating, or destroying function of renal nerves in a patient's kidney. Apparatus comprise a shaft adapted to be introduced into an interior of the kidney, typically the renal pelvis, and an effector on the shaft to exchange energy and/or deliver an active substance from the interior of the kidney through a wall of the renal pelvis into the nerves within the wall of the renal pelvis surrounding the renal blood vessels in the kidney. The effector will typically comprise an expandable member which can be expanded within the renal pelvis to engage an interior wall of the renal pelvis, for example, comprising a compliant balloon or mechanically expandable cage adapted to inflate/expand to occupy all or a substantial portion of the interior volume of the renal pelvis. The compliant balloon or other expandable structure can thus serve to position elements of the effector against the interior wall of the renal pelvis and/or to locate an internal mechanism within the effector in a predetermined position/geometry relative to the wall and nerves of the renal pelvis. Usually, the effector will be adapted to limit the exchange of energy and/or the delivery of active substances into regions of the kidney beyond the renal pelvis, such as the papillae, the pyramids, the parenchyma, and other sensitive structures of the kidney which could be damaged by the protocols herein and adversely impact kidney function. While the inflatable body or other portions of the effector could engage such sensitive structures, the effector will be designed so that energy exchange and/or active substance delivery avoid such sensitive structures, for example by placing external elements on the effector away from such sensitive structures.

In a series of alternative embodiments, the effector may comprise an energy transfer structure on an external surface of the expandable member or other effector body. For example, the energy transfer structure located externally on the effector may comprise electrodes for delivering radio frequency (RF) energy through the wall of the renal pelvis to the adjacent and surrounding renal nerves. Alternatively, the effector may comprise an energy delivery structure located internally to the effector, such as an antenna for delivering microwave energy through the wall and nerves of the renal pelvis to the surrounding renal nerves. Such internal energy delivery structures could also include ultrasound transducers for delivering ultrasound energy through the wall of the renal pelvis, for example high intensity focused ultrasound (HIFU) arrays. Still other internal energy delivery structures could comprise convective heat sources, including electrical resistance heaters, heated fluid exchange systems, and the like. Still other energy exchange structures include cryogenic other cooling structures, including both cryogenic fluid exchange structures and in situ cooling structures, such as gas expansion structures.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 7A-7D illustrate an energy delivery catheter having a plurality of tissue-penetrating electrodes which may be advanced into the wall of the renal pelvis adjacent to the ureteral os to deliver energy into the renal pelvis wall.

FIGS. 8A-8C illustrate an energy delivery catheter comprising a pair of bipolar electrodes and having vacuum ports to collapse the renal pelvis wall about the electrodes when the catheter is present in the renal pelvis adjacent to the ureteral os.

FIGS. 9A-9D illustrate an energy delivery catheter having a pair of expandable cages which may be deployed in the renal pelvis adjacent to the ureteral os to deliver energy into the renal pelvis wall.

FIGS. 10A-10D illustrate an energy delivery catheter having a pair of malecots which may be opened to deploy wire electrodes in the renal pelvis adjacent to the ureteral os to deliver energy into the renal pelvis wall.

DETAILED DESCRIPTION OF THE INVENTION

Figure 1:
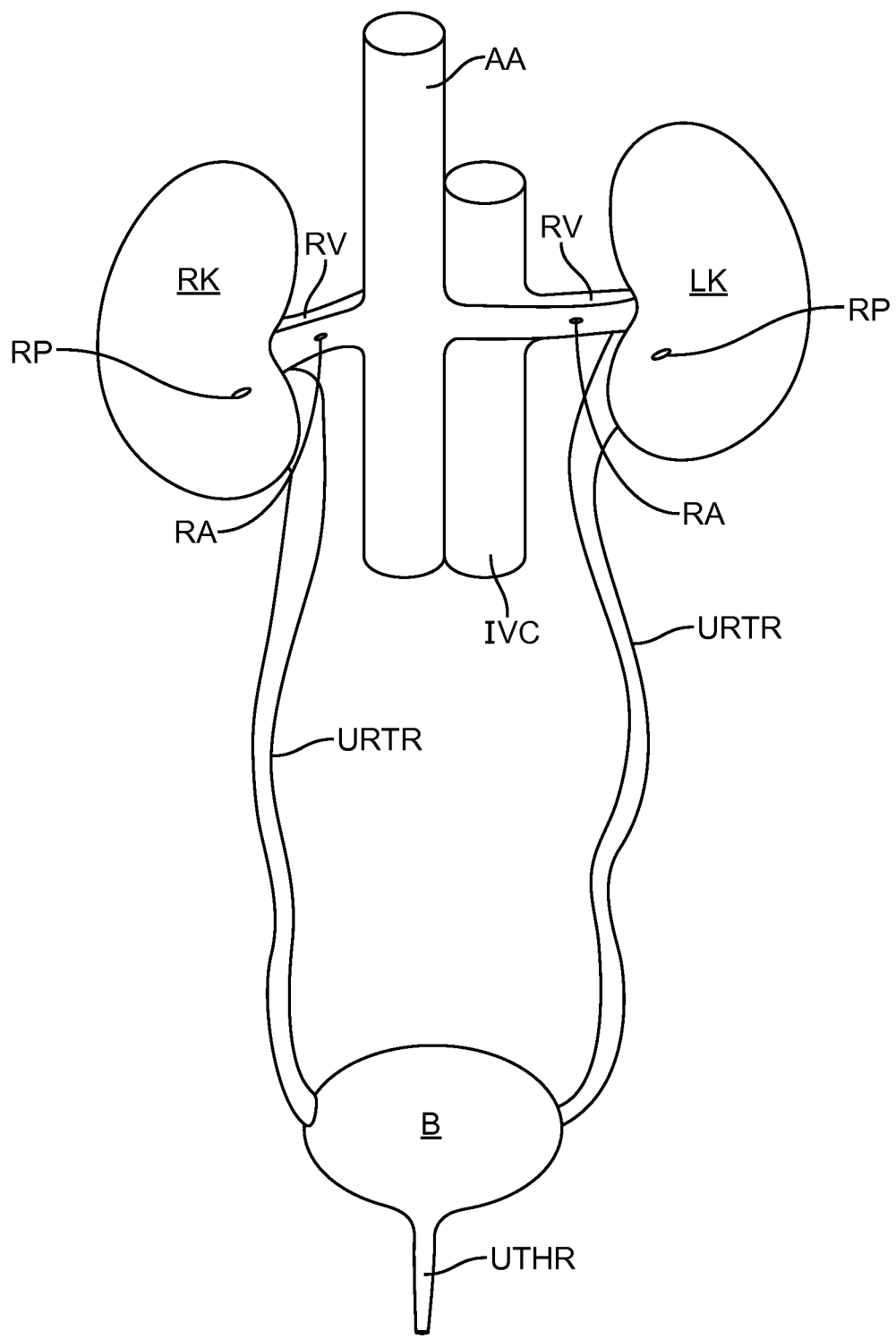
FIG. 1 is a diagrammatic illustration of a patient's urinary system.

A patient's urinary tract is diagrammatically illustrated in FIG. 1. The urinary tract includes the bladder B, which receives urine from the right and left kidneys RK and LK and drains the urine through the urethra UTHR. The kidneys each receive oxygenated blood through the renal artery RA from the abdominal aorta AA and blood from the kidneys is returned through the renal vein RV to the inferior vena cava IVC. Of particular interest to the present invention, the urine which is processed in the kidney is received in an interior cavity of each kidney referred to as the renal pelvis RP which acts as a funnel and delivers the urine into the top of the ureter URTR. The methods and protocols of the present invention will be performed within the interior of the renal pelvis RP in order to treat the renal nerves within the walls of the renal pelvis as well as the nerves surrounding the renal arteries within the adventitia and adipose tissue and to a lesser extent surrounding the renal veins which branch from the main renal artery and renal vein within the tissue of the kidney.

Figure 2B:
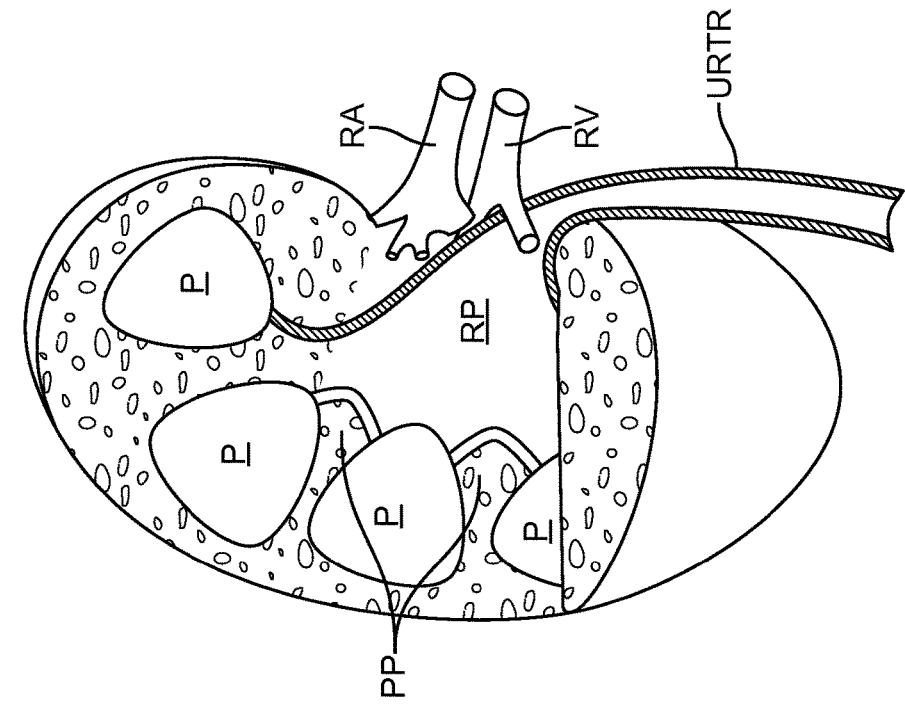
FIGS. 2A and 2B are partially broken-away illustrations of a patient's kidney showing the renal pelvis and other structures.
Figure 2A:
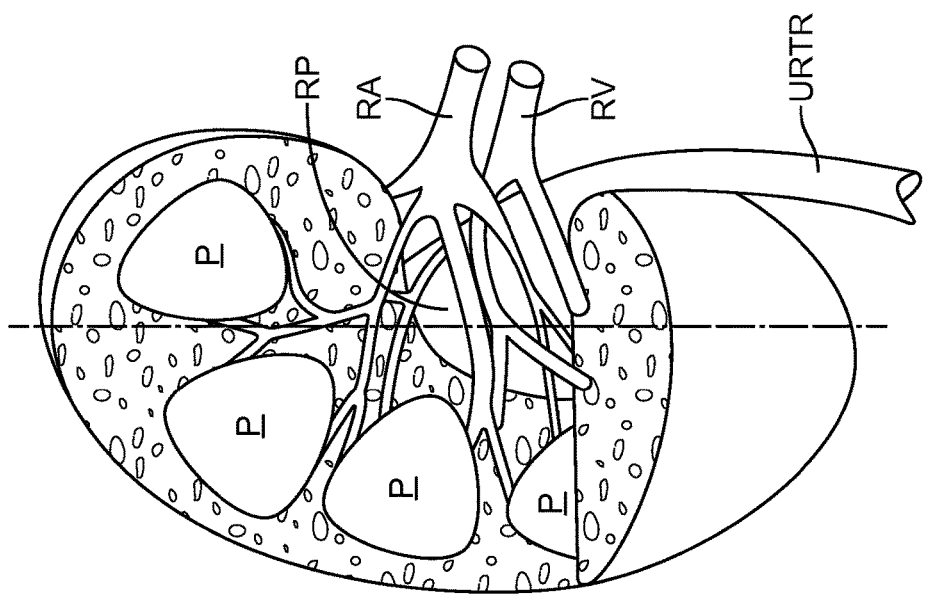

Referring now to FIGS. 2A and 2B, the right kidney RK is shown in section to expose the renal pelvis RP and other internal structures of the kidney. As shown in FIG. 2A, the renal pelvis is a funnel-shaped extension of the upper and of the ureter URTR and is surrounded by the branching portions of the renal artery RA and the renal vein RV, both of which branching structures extend into the body of the kidney and surround the pyramids P and other structures, including the papillae PP. The branching structures of the renal artery RA and renal vein RV as well as the anterior wall of the renal pelvis are removed in FIG. 2B to show the interior of the renal pelvis which is the target location for the therapies of the present invention.

Figure 3:
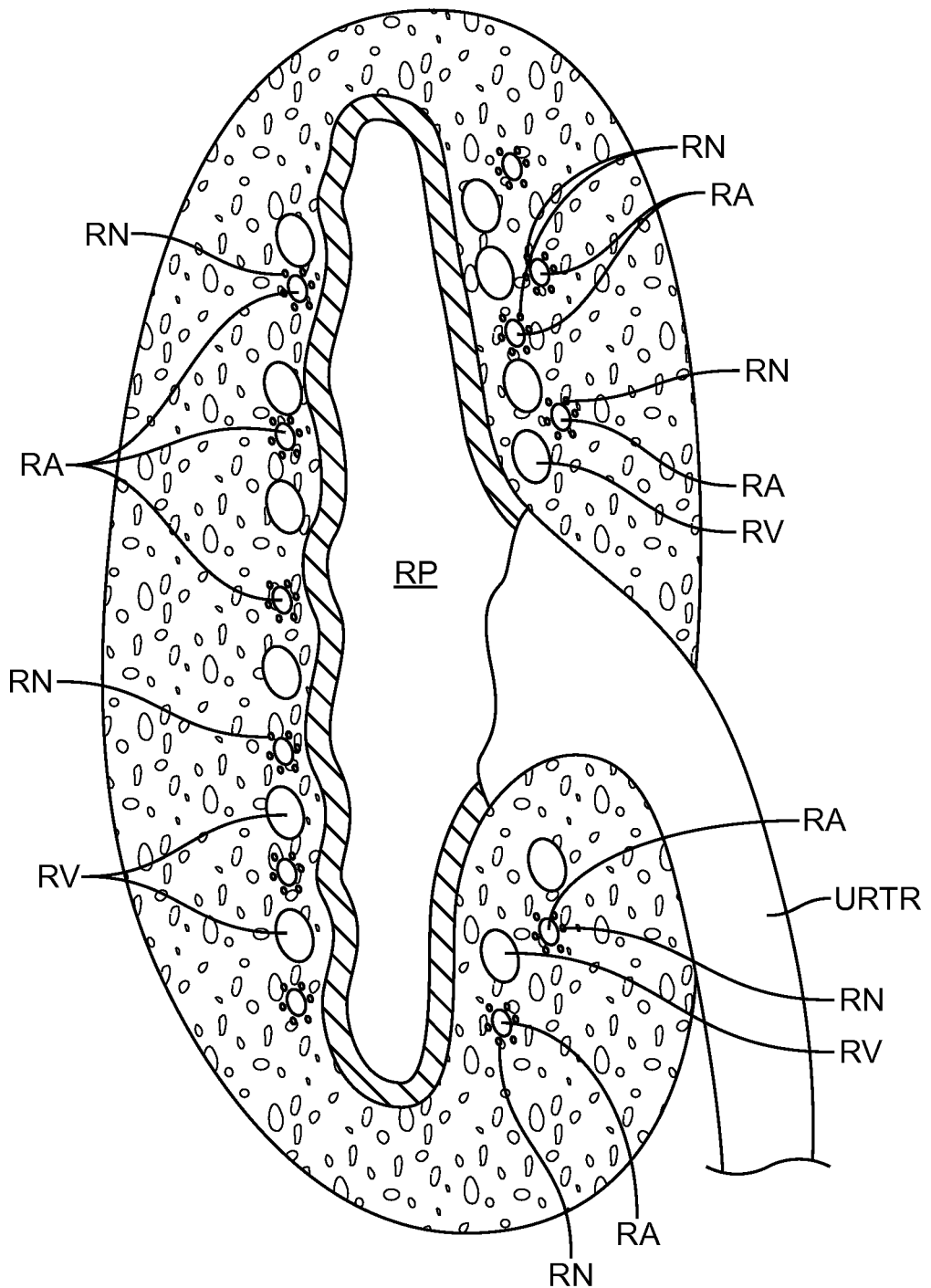
FIG. 3 is a cross-sectional view of the patient's kidney taken along line 3-3 of FIG. 2A.
Figure 3A:
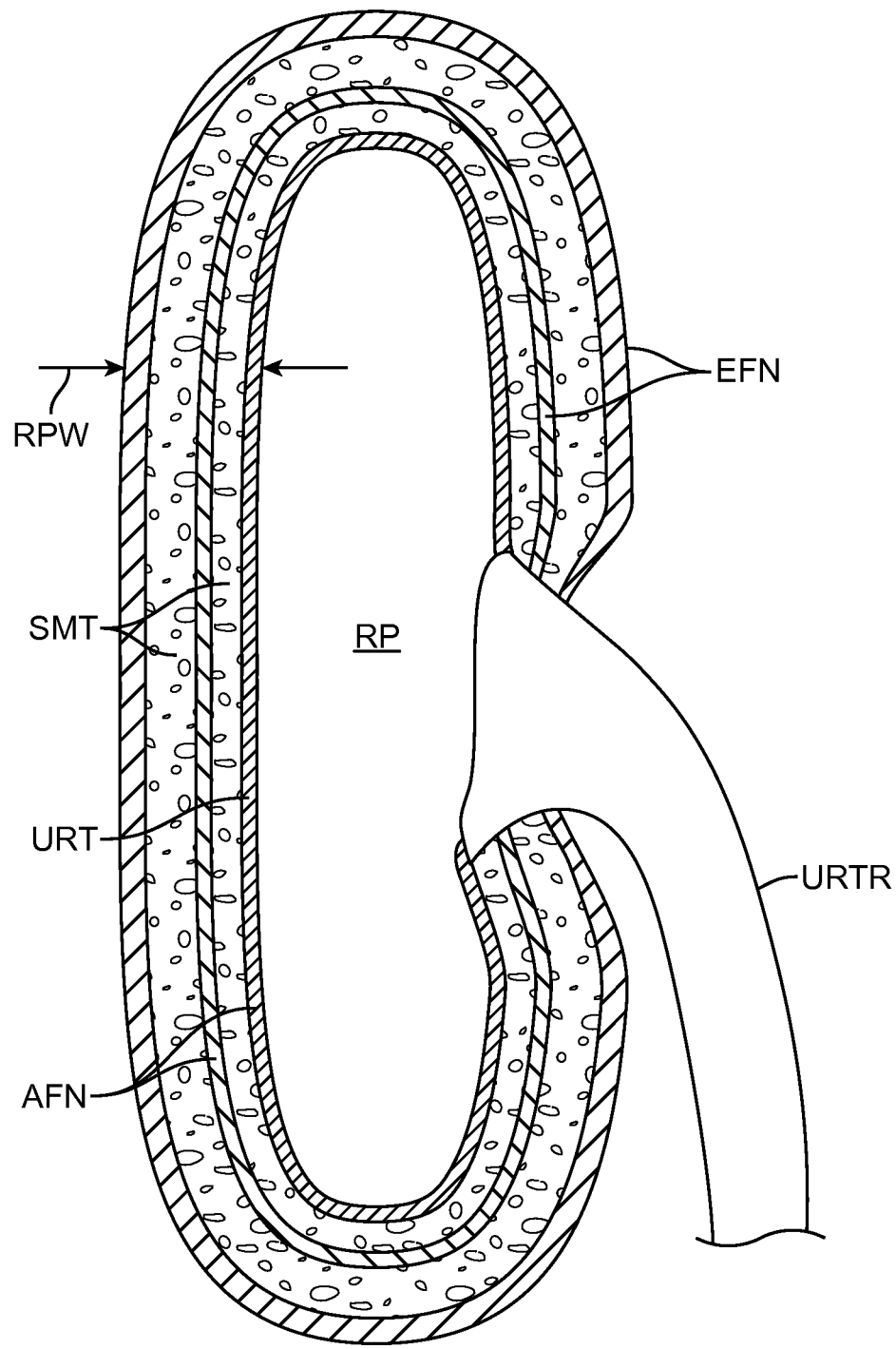
FIG. 3A shows the structure and location of renal nerves within the muscle layers, endothelium and submucosa of the renal pelvis. The afferent nerves originate and are mostly contained within the wall of the renal pelvis. They have a direct effect on the efferent sympathetic nerves and are responsible for sympathetic muscle tone and vasoconstriction.

As further shown in FIG. 3 which is a cross-sectional view taken along line 3-3 of FIG. 2A, the renal nerves RN surround the renal blood vessels, particularly the renal arteries RA, extending adjacent to and surrounding the outer wall of the renal pelvis RP in a tissue bed surrounding the renal pelvis. As shown in FIG. 3A, the renal nerves follow the arteries and then divide. A portion of the divided nerves enter the renal pelvic wall RPW where they intertwine with the afferent nerves AFN that are located within the smooth muscle layers, endothelium and submucosa SML of the renal pelvis. The afferent nerves AFN originate and are mostly contained within an interior wall of the renal pelvis adjacent to the urothelium URT. The afferent nerves have a direct effect on the efferent sympathetic nerves EFN (which are generally located nearer the exterior surface of the renal pelvis wall RPW than are the afferent sensory nerves AFN) and are responsible for sympathetic muscle tone and vasoconstriction. It is the renal nerves shown in FIGS. 3 and 3A, and in particular the sensory afferent nerves AFN, which are typically but not exclusively the target structures to be treated by the methods and apparatus of the present invention.

Figure 4A:
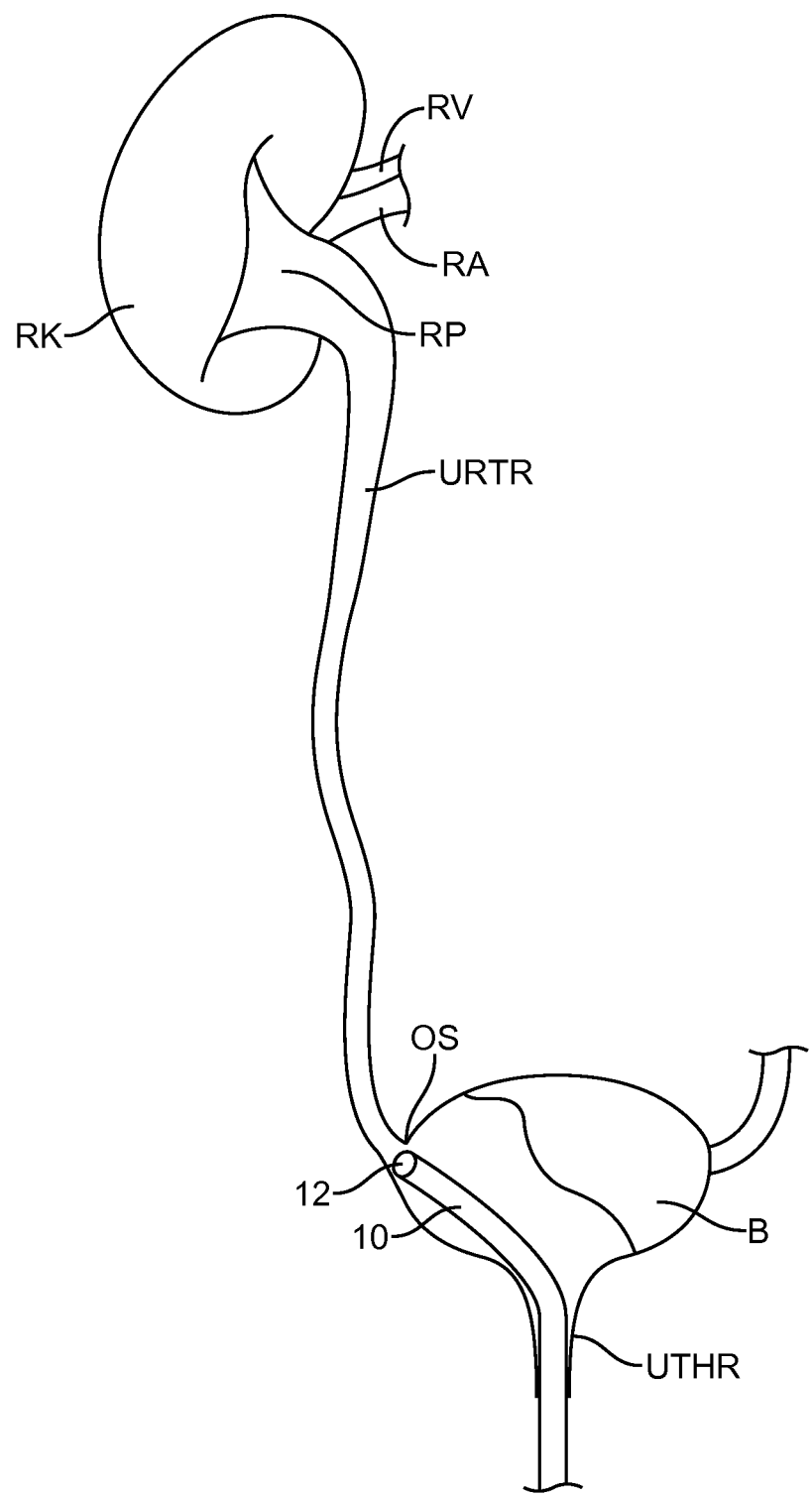
FIGS. 4A through 4C illustrate access and treatment of a patient's renal pelvis according to the principles of the present invention.
Figure 4B:
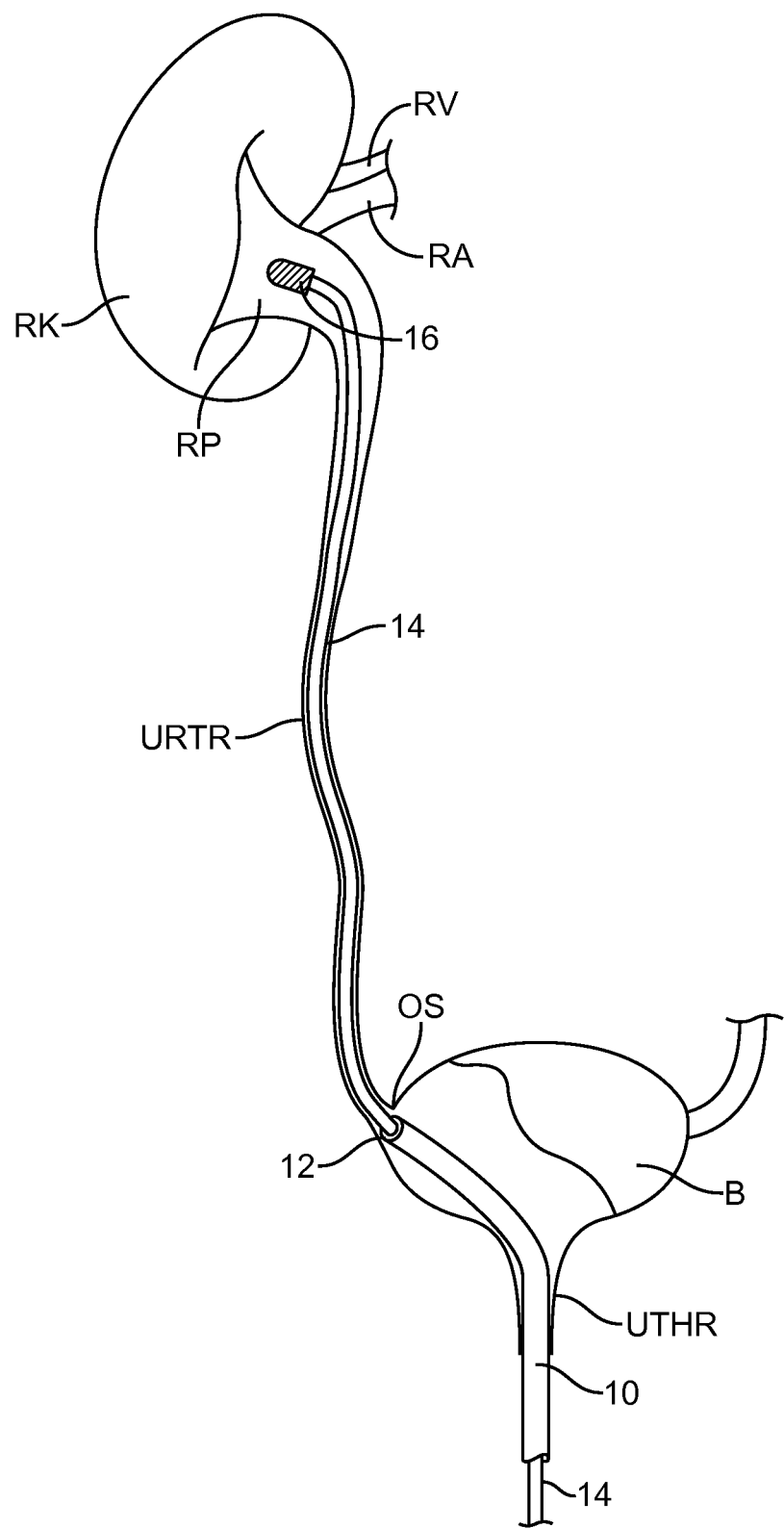
Figure 4C:
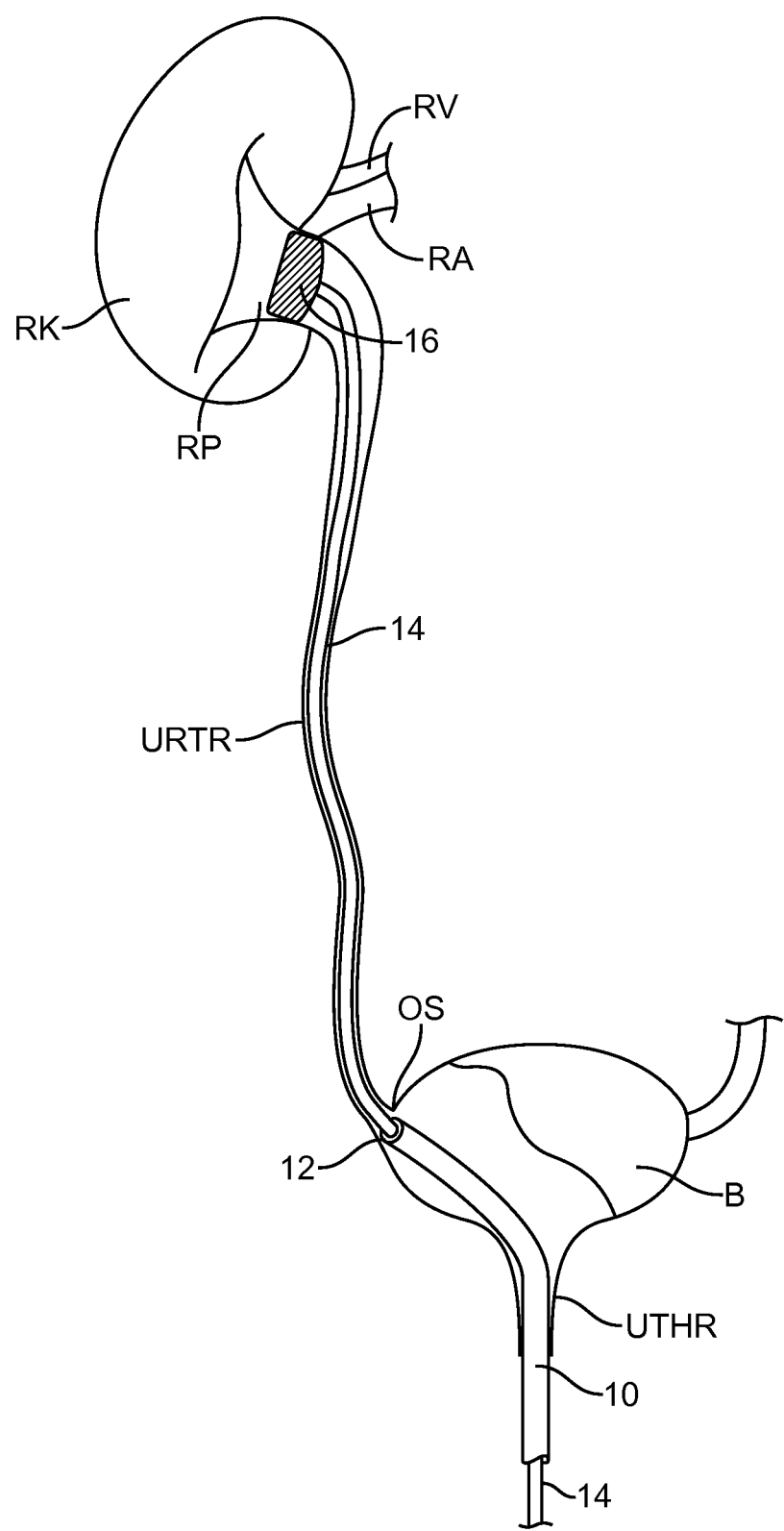

Referring now to FIGS. 4A through 4C, a first exemplary protocol for accessing and treating the renal nerves in the kidney will be described. Initially, a guide or other tubular catheter 10 is advanced through the urethra UTHR to position a distal port 12 adjacent the os OS at the lower end of the ureter URTR. Additionally or alternatively, a guidewire may be employed.

As shown in FIG. 4B, a treatment catheter 14 is then advanced through the guide catheter 1 (optionally over a guidewire), out of port 12, and into a lumen of the ureter URTR. An effector 16 at the distal end of the treatment catheter 14 is advanced into the renal pelvis RP, optionally under fluoroscopic and/or ultrasound guidance in a conventional manner.

Once in the renal pelvis RP, the effector 16 will be deployed in order to treat the renal nerves in accordance with the principles of the present invention. For example, the effector may comprise an expandable balloon or other structure which is expanded or inflated within the renal pelvis to engage the interior walls of the pelvis as shown FIG. 4C. Any one of a variety of energy exchange devices or substance delivery devices may then be employed to exchange energy or deliver the substances through the wall of the renal pelvis to treat the nerves embedded within the walls of the renal pelvis as well as the nerves embedded in the tissue surrounding the renal pelvis.

Figure 5A:
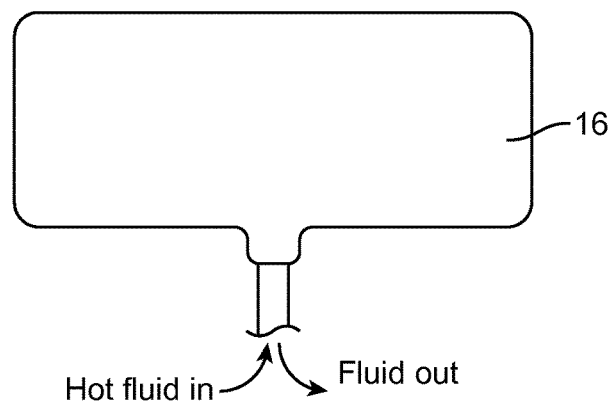
FIGS. 5A through 5F illustrate different effector designs that can be used for treating the renal nerves in accordance with the principles of the present invention.
Figure 5B:
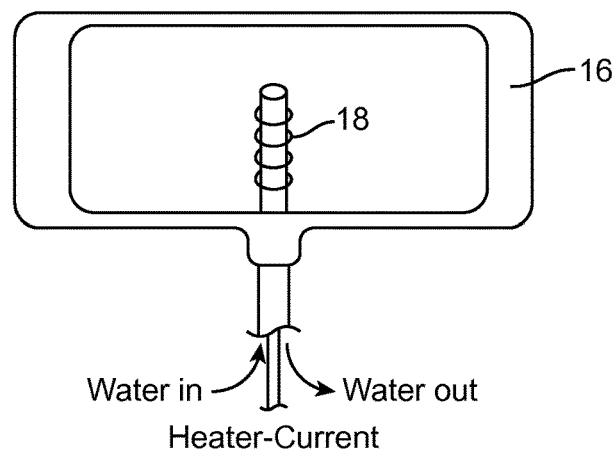

As shown in FIG. 5A, for example, the inflated or expanded effector 16 can be used to deliver convective heat through the wall of the renal pelvis, for example by delivering an externally heated fluid into the interior of the effector and removing the fluid from the interior to recirculate the hot fluid. As shown in FIG. 5B, it would also be possible to use an electrical resistance or other heater 18 which is positioned within the effector 16 in order to heat a fluid in situ where the fluid would not necessarily be recirculated. Typically, continuous irrigation will be provided through the catheter to cool the electrodes which in turn reduces damage to the adjacent tissue in contact with the electrode.

Figure 5C:
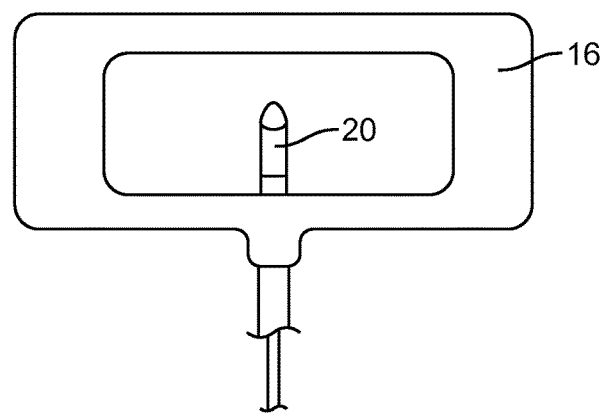

As shown in FIG. 5C, energy can be delivered in other ways, such as using a microwave antenna 20 which is positioned by the effector 16 to deliver microwave energy through the wall and into the nerves within the renal pelvis. Both the dimensions and geometry of the effector 16 as well as the transmission characteristics of the antenna 20 can be configured in order to selectively deliver the microwave energy into the tissue to achieve the targeted heating.

Figure 5D:
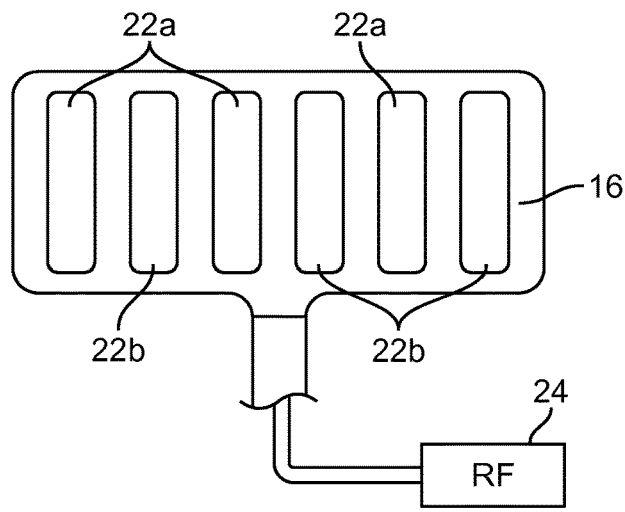

Still another alternative energy delivery mechanism is illustrated in FIG. 5D where bipolar electrodes 22a and 22b are arranged on the exterior of the effector 16 surface and connectible to an external radiofrequency generator 24 to deliver bipolar radiofrequency energy to the tissue. Again, the dimensions of the electrodes, spacing, and other system features can be selected to deliver energy to a proper depth in wall of the renal pelvis as well as to the tissue beds surrounding the renal pelvis.

Figure 5E:
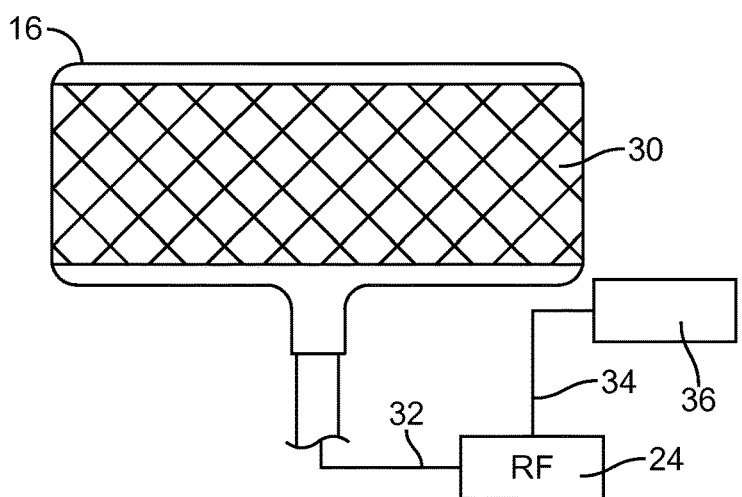

As shown in FIG. 5E, a single monopolar electrode 30 may be provided on the exterior of the effector 16 where one pole 32 of the RF generator 24 connected to the electrode on the effector and the other pole 34 connected to an external pad 36 which will be placed on the patient's skin, typically on the lower back.

Figure 5F:
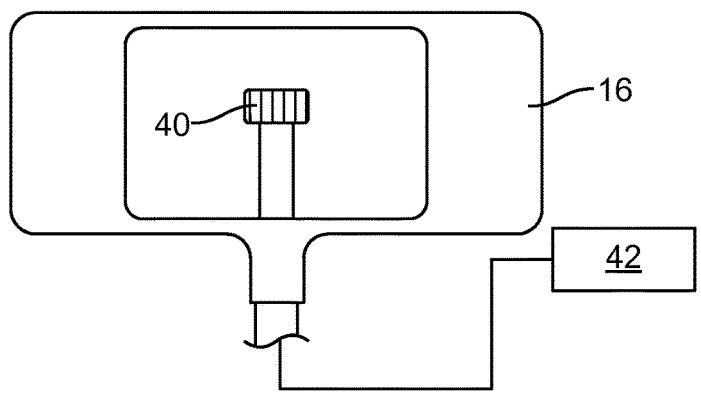

Still further, effector 16 construction shown in FIG. 5F includes an ultrasound phased array 40 positioned within the interior of the effector and connected to an external ultrasound generator 42. The ultrasound phased array 40 will typically be constructed to provide high intensity focused ultrasound (HIFU) in order to selectively deliver energy across the wall of the renal pelvis and into the tissue beds surrounding the pelvis in order to heat the tissue and treat the renal nerves in accordance with the principles of the present invention.

Figure 6A:
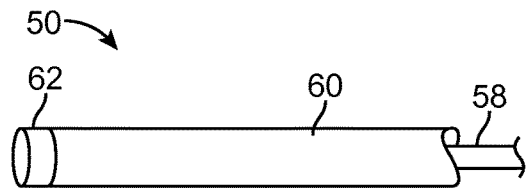
FIGS. 6A-6D illustrate an energy delivery catheter having an expandable cage which is deployed in the renal pelvis adjacent to the ureteral os to deliver energy into the renal pelvis wall.
Figure 6B:
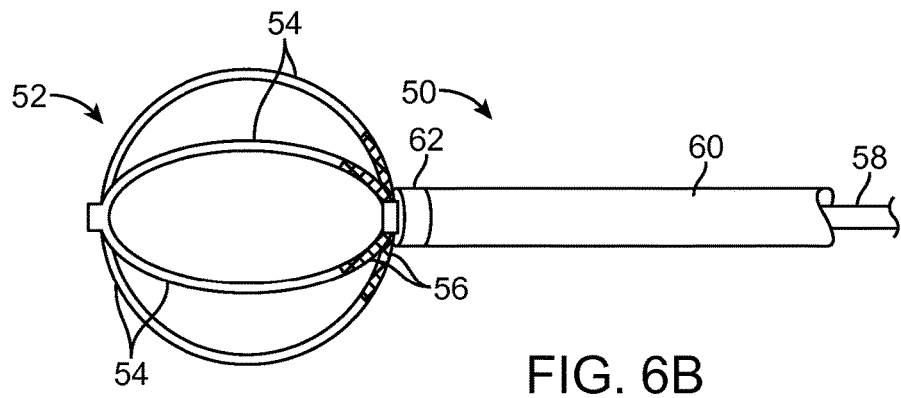
Figure 6C:
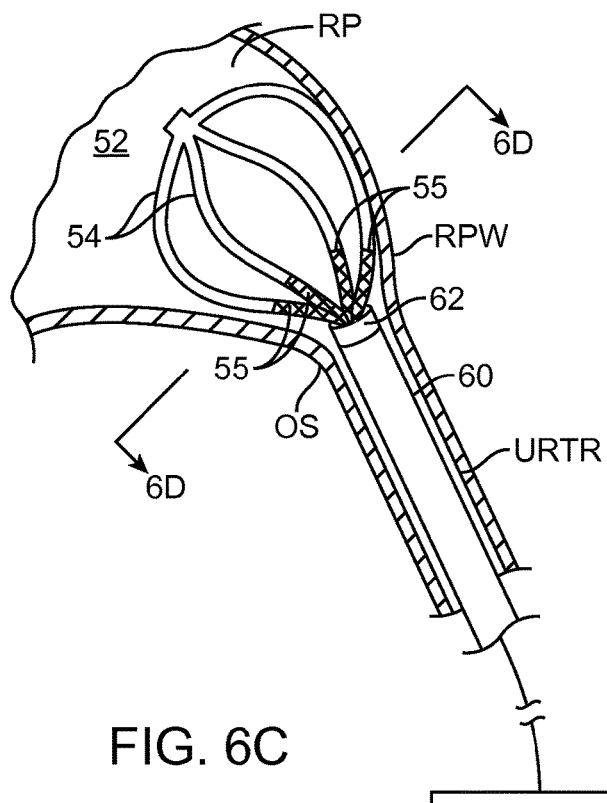
Figure 6D:
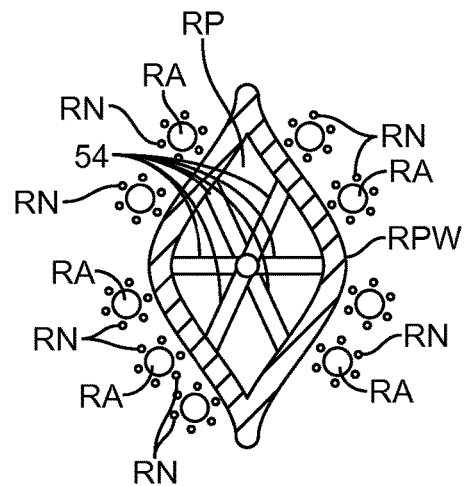

Referring now to FIGS. 6A-6D, an expandable cage catheter cage 50 comprises an expandable cage structure 52 including a plurality of electrode elements 54. The electrode elements will typically be formed from a shape memory alloy, such as nitinol, and will usually be electrically conductive along their entire lengths. A proximal portion of each electrode, however, will usually be covered with a layer of insulation 55 in order to inhibit energy delivery to the upper region of the ureter URTR through which the catheter is introduced. The catheter 50 further includes an inner shaft 58 and an outer sheath 60, where the outer sheath may be distally advanced over the expandable cage structure 52 in order to collapse the cage structure for delivery, as shown in FIG. 6A. By retracting the sheath 60 relative to the inner shaft 58, the cage 52 may be deployed as shown in FIG. 6B. After the catheter 50 is introduced through the ureter URTR, as shown in FIG. 6C, the sheath may be retracted in order to deploy the cage structure 52 within the renal pelvis RP adjacent to the ureteral os OS. The portions of the electrode elements 54 adjacent to the os will be insulated so that energy is preferentially delivered a short distance above the os in order to avoid damage to the ureter and other sensitive structures. The energy delivered through the electrode elements 54 will pass through the wall RPW of the renal pelvis in order to treat the renal nerves (RN), as shown in FIG. 6D. A radiopaque marker 62 can be provided at or near the distal end of the sheath 60 to assist in positioning the catheter 50 at or above the os under fluoroscopic imaging.

Referring now to FIGS. 7A-7D, a penetrating electrode catheter 70 includes a plurality of tissue-penetrating electrodes 72 deployed from an inner shaft 74 and having an outer sheath 76 reciprocatably mounted thereover. The outer sheath 76 has a radiopaque marker 78 at its distal end (for positioning in the ureter URTR) and may be selectively retracted from a distal tip 80 of the inner shaft 74 in order to deploy the tissue-penetrating electrodes 72, as shown in FIG. 7B. Usually, the catheter 70 will have a port 82 opening to an inner lumen (not shown) to allow advancement over a guidewire GW, as shown in FIGS. 7A and 7C.

After the marker 78 of the catheter 70 is positioned at or just above the ureteral os OS, as shown in FIG. 7C, the inner shaft 74 may be advanced to deploy the electrodes 72 into the wall RPW of the renal pelvis RP. RF energy is then delivered from the power supply 84 in order to treat the renal nerves RN which surround the renal pelvis wall RPW as shown in FIG. 7D.

Referring to FIGS. 8A-8C, a bipolar electrode 90 having a pair of axially spaced-apart electrodes 94 comprises a catheter shaft 92 having a plurality of vacuum ports 96 disposed between the electrodes. The vacuum ports 96 communicate with an inner lumen (not illustrated) which allows a vacuum to be drawn through the ports in order to partially collapse the renal pelvis, as shown in FIGS. 8B and 8C. After the catheter 50 is advanced to a location where the proximal-most electrode 94 is advanced past the ureteral os OS, as shown in broken line in FIG. 8B, a vacuum may be drawn in the lower portion of the renal pelvis RP to collapse the walls, as shown in full line in both FIGS. 8B and 8C. An external power supply/controller 98 may include both a vacuum source and a radio frequency power source for connection to the catheter 90. After the wall of the renal pelvis is collapsed, radiofrequency energy will be delivered through the electrodes 94 from the power supply 98 in order to treat the renal nerves RN.

Further referring to FIGS. 9A-9D, a multiple cage catheter 100 has a plurality of individual cages 102 (with two cages illustrated) mounted on an inner shaft 104. The inner shaft terminates at a distal tip 106 having a port 107 which can receive a guidewire GW (FIG. 9) through a central guidewire lumen (not illustrated). The cages 102 are self-expanding, typically being formed from nitinol or other electrically conductive shape memory material, and will be collapsed by an outer sheath 108 which may be advanced over the cages, as shown in broken line in FIG. 9A, or be retracted to allow the cages to expand as shown in full line in FIG. 9B. The catheter 100 may be advanced through the ureter URTR, as shown in FIG. 9C, where the sheath 108 is then retracted to allow the electrode cages 102 to expand and engage the wall of the renal pelvis RP, as shown in FIG. 9D. Each cage 102 will have a plurality of active electrode regions 110 which are usually formed by covering the non-active regions of the cage (i.e. everything except the active regions at the centers) with an insulating layer or material. After the cages 102 are deployed in contact with the inner surface of the renal pelvis wall RPW, radiofrequency energy may be delivered through power supply 112.

Referring now to FIGS. 10A-10D, a wire electrode catheter 120 comprises a catheter shaft 122 having a distal end 124. A first set of four axial slits 126a are circumferentially spaced-apart about the tubular wall of the catheter shaft 122, and a second set of four axial slits 126b are also circumferentially spaced apart about the catheter shaft at a region just proximal to the first set. Only four of the two slits 126a and two of the four slits 126b are visible with the remaining two of each set being hidden on the far side of the catheter shaft 122. By axially tensioning the catheter shaft 122, for example by pulling on a cable 127 which is attached at the distal end 124 of the shaft 122, the shaft may be for shortened causing the sections between adjacent slits to project outwardly to form malecot structures 128, as best seen in FIG. 10B. Electrode wires 130 extend between the axially aligned sections of the first and second malecots so that the wires are advanced radially outwardly when the malecots are deployed by foreshortening the catheter shaft 122. The wires 132 are continuous and extend into an inner lumen of the shaft and exit the shaft at a proximal end thereof and are connected to a power supply 134.

In order to confirm proper deployment of the electrode wires 130, radiopaque markers 136 are formed distally to, between, and proximally to the slit-malecot structures 128, so that the markers will appear to move together under fluoroscopic observation as the malecots are deployed by pulling on cable 127.

As shown in FIG. 10C, the deployable structure of the catheter 120 is positioned just beyond the ureteral os OS to deploy the malecot structures 128 radially outwardly as shown best in Fig. D. The wires 130 between the malecots 128 will engage the walls of renal pelvis RP above the os OS, and energy may be applied from a power supply 134. Optionally thermocouples 132 will be formed at the radially outward tips of each malecot 128 such that they can penetrate the wall of the renal pelvis in order to monitor temperature during treatment. As before, energy will be delivered in order to inhibit or modulate the function of the renal nerves RN surrounding the renal pelvis wall RPW, as shown in FIG. 10D While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for inhibiting the function of renal nerves in a kidney of a patient suffering from hypertension, said method comprising:

introducing an effector comprising an array of electrodes through the urinary tract into an interior of the kidney or an upper region of an adjacent ureter;

expanding the array of electrodes within the kidney or upper region of an adjacent ureter to engage an interior wall of the renal pelvis;

delivering radiofrequency energy to the array of electrodes through the interior wall of the renal pelvis to afferent sensory nerves within the wall of the renal pelvis, wherein a temperature of a tissue bed in the wall of the renal pelvis surrounding the afferent sensory nerves is raised to a temperature in a range from 45° C. to 60° C.; and irrigating the expanded electrodes to maintain a temperature of the papillae, the parenchyma, and the pyramids in the kidney below 45° C., wherein blood pressure of the patient is reduced.

2. A method as in claim 1, wherein the effector is disposed on a urinary catheter and the urinary catheter is advanced through the urethra, bladder, and ureter to reach the renal pelvis.

3. A method as in claim 1, wherein the radiofrequency energy is delivered for a time in a range from 1 to 2 minutes.

* * * * *